United States Patent [19]
Cerny

[11] Patent Number: 5,958,790
[45] Date of Patent: Sep. 28, 1999

[54] SOLID PHASE TRANSVERSE DIFFUSION ASSAY

[75] Inventor: Erich H. Cerny, Baltimore, Md.

[73] Assignee: Nycomed Imaging AS, Oslo, Norway

[21] Appl. No.: 08/447,043

[22] Filed: May 22, 1995

Related U.S. Application Data

[63] Continuation of application No. 08/022,853, Feb. 25, 1993, abandoned, which is a continuation of application No. 07/587,510, Sep. 24, 1990, abandoned, which is a continuation of application No. 06/895,859, Aug. 12, 1986, abandoned, which is a continuation-in-part of application No. PCT/US85/02534, Dec. 19, 1985, which is a continuation-in-part of application No. 06/761,961, Aug. 2, 1985, abandoned, which is a continuation-in-part of application No. 06/684,059, Dec. 20, 1984, abandoned.

[51] Int. Cl.$^6$ ............... G01N 33/543; G01N 33/558; G01N 33/566
[52] U.S. Cl. ............... 436/501; 422/56; 422/58; 422/60; 435/4; 435/5; 435/6; 435/7.1; 435/7.4; 435/7.5; 435/287.2; 435/287.8; 435/805; 435/970; 436/514; 436/518; 436/524; 436/525; 436/530; 436/807; 436/828
[58] Field of Search ............... 435/4, 5, 6, 7.1, 435/7.4, 7.5, 805, 970, 287.2, 287.8; 436/501, 524, 518, 525, 530, 807, 828, 514; 422/56, 58, 60

[56] References Cited

U.S. PATENT DOCUMENTS

| | | | |
|---|---|---|---|
| 3,810,739 | 5/1974 | Nussbaum | 435/805 X |
| 4,168,146 | 9/1979 | Grubb et al. | |
| 4,200,508 | 4/1980 | Hirai | 436/514 |
| 4,313,734 | 2/1982 | Leuvering | 436/525 X |
| 4,366,241 | 12/1982 | Tom et al. | 435/7.2 X |
| 4,435,504 | 3/1984 | Zuk et al. | 435/7.91 |
| 4,446,238 | 5/1984 | De Mey et al. | 436/527 |
| 4,447,526 | 5/1984 | Rupchock et al. | 436/535 X |
| 4,459,358 | 7/1984 | Berke | 436/810 X |
| 4,517,288 | 5/1985 | Giegel et al. | 436/514 X |
| 4,582,699 | 4/1986 | Murray | 436/511 X |
| 4,587,102 | 5/1986 | Nagatoma et al. | 422/56 |
| 4,631,174 | 12/1986 | Kondo | 435/805 X |
| 4,632,901 | 12/1986 | Valkirs et al. | 436/824 X |
| 4,666,863 | 5/1987 | Edwards et al. | 436/514 |
| 4,670,381 | 6/1987 | Fricker et al. | |
| 4,690,890 | 9/1987 | Loor et al. | 436/531 X |
| 4,703,017 | 10/1987 | Campbell et al. | 436/518 X |
| 4,752,562 | 6/1988 | Sheiman et al. | 435/5 |
| 4,770,853 | 9/1988 | Bernstein | 422/58 |
| 4,774,174 | 9/1988 | Giegel et al. | 435/5 |
| 4,775,636 | 10/1988 | Moeremans et al. | 436/518 |
| 4,786,606 | 11/1988 | Giegel et al. | 436/500 |
| 5,006,464 | 4/1991 | Chu et al. | 435/7.1 |

FOREIGN PATENT DOCUMENTS

| | | |
|---|---|---|
| 2057126 | 3/1981 | United Kingdom . |
| 07900044 | 2/1979 | WIPO . |

*Primary Examiner*—David Saunders
*Attorney, Agent, or Firm*—Sughrue, Mion, Zinn, Macpeak & Seas, PLLC

[57] ABSTRACT

The present invention relates to a method and kit for carrying out a qualitative or semi-quantitative assay. The invention uses a multi-layer device including an an uppermost cover layer of a water-impermeable material having a hole therein with a diameter of approximately 1–5 mm, an intermediate insoluble porous support layer having a first substance bound thereon in a reaction zone, the hole exposing at least a part of the reaction zone, and a layer of a hydrophilic material in contact with and positioned on the side of the insoluble porous support layer opposite the side with the cover layer. The device permits transverse, but not substantial radial, diffusion of liquid through the reaction zone. Approximately 1–50 $\mu$l of a test sample and a second substance are applied to the reaction zone through the hole. A colloidal gold label is attached to the second substance. The presence or approximate quantity of the immobilized second substance is assessed by the presence, for a qualitative determination, or intensity for a semi-quantitative determination, of a color signal generated by the immobilized colloidal gold label in the part of the reaction zone exposed by the hole.

14 Claims, 6 Drawing Sheets

SOLID PHASE TRANSVERSE DIFFUSION ASSAY

CROSS-REFERENCE TO RELATED CASES

This application is a continuation of U.S. application Ser. No. 08/022,853, filed Feb. 25 ,1993 and now abandoned, which is a continuation of U.S. application Ser. No. 07/587, 510, filed Sep. 24, 1990 and now abandoned, which is a continuation of U.S. application Ser. No. 06/895,859, filed Aug. 12, 1986 and now abandoned, which is a continuation-in-part of PCT application PCT/US85/02534, filed Dec. 19, 1985, which is a continuation-in-part of U.S. application Ser. No. 06/761,961, filed Aug. 2, 1985 and now abandoned, which is a continuation-in-part of U.S. application Ser. No. 06/684,059, filed Dec. 20, 1984 and now abandoned.

TECHNICAL FIELD

This invention relates to the quantitative and qualitative assay of small amounts of substances in a solution and more particularly to the rapid and simple identification and quantification of substances in solution by a novel solid phase diffusion assay technique. The novel assay may be adapted to rapidly and quantitatively determine the concentration of proteins, hormones, drugs, polypeptides, vitamins, glycosides and the like. The present invention further relates to a kit for effecting such quantitative measurements and to certain novel components of such kits and for use in the novel assay.

BACKGROUND OF THE INVENTION

There is a continuing need for an inexpensive, easy to perform method of detecting substances that are present in fluids at concentrations on the order of $1 \times 10^{-6}$ grams or less. Prior art methods capable of accurately detecting a substance in a fluid at these concentrations are cumbersome, expensive and require long periods of time to perform. In addition, expensive and complicated equipment is required to perform these prior art methods.

There are many prior art assay methods designed to detect the presence of soluble substances in serum and other media of biological importance. For substances that have biological activity, one can simply measure the activity in the biological fluid to detect the presence of the substance. For example, one can measure the presence of the enzyme acid phosphatase in blood serum by adding a substrate of acid phosphatase enzyme such a p-nitrophenyl phosphate and incubating the solution for a period of time. If the enzyme is present in the blood, the solution will turn yellow as the substrate is hydrolyzed by the enzyme to phosphate and p-nitrophenol. However, there are many problems associated with this type of assay. For example, the substance to be assayed must have a biological activity that can be measured. Often the measurement of biological activity can be cumbersome and very time consuming. Furthermore, the activity of the enzyme may be inhibited by the presence of an inhibitor. If such an inhibitor is present, a falsely low activity will be measured. In addition the enzyme may be present in the fluid but may be inactive.

Another method of measuring the presence of trace substances in biological fluids is a process known as chromatography. There are many different types of chromatography. Thin layer chromatography, in combination with mass spectroscopy or gas phase chromatography, has been used to isolate and quantify a particular substance in biological fluids. However, thin layer chromatography has a number of deficiencies such as being slow, being subject to a wide range of interfering materials, and suffering from severe fluctuations inreliability.

Liquid chromatography is another method of isolating materials from biological fluids. In this method, advantage is taken of particular molecule's physical properties, such as size or charge. However, one still must utilize a method of analyzing the particular substance after it is isolated. This can be done by measuring biological activity, absorbance characteristics, mass spectroscopy, or by further separation analysis.

Another method that takes advantage of molecular charge and size is gel electrophoresis. In this method, a biological sample is placed on a porous gel. The sample and the gel are then subjected to an electrical field causing the ample to migrate through the gel. The rate of migration is dependent upon the charge and on the size of the molecule. In this way, different molecules can be separated and isolated.

There are many problems with chromatographic and electrophoretic methods for identification of substances. One of the problems is in identifying the substance after it has been isolated. In order to identify the isolated substance, one must perform another procedure such as measurement of biological activity, analysis by mass spectroscopy or identification by other methods, such as immunological methods. An electrophoresis or chromatography procedure is a time consuming process taking several hours to several days. In addition, the equipment used in these procedures is expensive and requires an experienced technician to perform the analysis.

Another method of identifying trace amounts of a particular substance in a solution is through immunological techniques. All immunological procedures use an antigen, and an antibody which is specific for the antigen. Prior art immunological methods include immunological precipitation in which the antibody combines with an antigen for which the antibody is specific. The resulting complex precipitates out of solution forming a visible precipitate.

Agglutination is another prior art method of detecting small concentrations of a particular substance. In agglutination, a body, such as a red blood cell or a bacteria, is reacted with antibodies that are specific for an antigen on the surface of the body. As the antibodies react with the surface antigens, the cells agglutinate forming a dense, visible clump.

The procedures of immunoprecipitation and immunoagglutination suffer from a general lack of sensitivity. In addition, the procedures require the antigen to have multiple antibody binding sites so that the antibodies may crosslink the antigens causing the precipitation or agglutination. The process of immunoprecipitation requires several hours to several days to complete thereby making the procedure impractical for many situations where the identification or quantification of a particular substance must be performed quickly.

The problem of lack of precision by the above described procedures was overcome by the procedure known as radioimmuno assay. In this procedure, the antigen to be measured is "labeled" with a radioactive element to form a radioactive analogue. Radioactive isotopes that are commonly used in radioimmunoassays are shown in Table I.

TABLE I

Radioactive Isotopes used for Tagging Biological Materials

| Isotope | Specific Activity of Pure Isotope (Curies per mole) | Half-life | |
|---|---|---|---|
| $C^{14}$ | $6.25 \times 10^1$ | 5230 | years |
| $H^3$ | $2.91 \times 10^4$ | 12.3 | years |
| $S^{35}$ | $1.50 \times 10^6$ | 87 | days |
| $I^{125}$ | $2.18 \times 10^6$ | 60 | days |
| $P^{32}$ | $3.16 \times 10^6$ | 14.3 | days |
| $I^{131}$ | $1.62 \times 10^7$ | 8.1 | days |

By mixing an antibody with solutions of a hapten or antigen to be analyzed, and with the radioactive antigen analogue, the radioactive analogue will be prevented from binding to the antibody to an extent directly proportional to the concentration of the hapten or antigen in the solution. By then separating and assaying the free radioactive analogue from the antibody bound radioactive analogue, one can indirectly determine the amount of hapten or antigen in the original-solution.

However, the use of radioisotopes in such an assay is a potential health hazard and, furthermore, the instrumentation required for radioimmunoassay is relatively sophisticated and expensive. Another problem with the radioimmunoassay is in labeling the antigen or antibody. The isotopes that are most commonly used are those with a short half-life. These include Iodine-131 and Iodine-125. Because these isotopes have such a short half-life (8.1 days and 60 days, respectively), the labeled component of an assay must periodically be replaced with new product. In addition, a standard curve must be prepared with each unknown sample since the specific activity of the isotope is constantly decreasing. A further problem with some labeled components is autodegradation. The isotopes that are commonly used to label the compounds are relatively strong radiation emittors and can cause the compounds to which they are attached to be degraded Finally, with the advent of increasing number of government regulations concerning the disposal of radioactive wastes, disposing of the radioactive isotopes used in radioimmuno assays has become an increasingly difficult and expensive problem.

Enzyme immunoassays overcome the above problems and in addition, have the unique advantage of potential amplification of the measured activity. (The field of enzyme immunoassays has been extensively reviewed in *Developments in Immunology*, Vol. 18, Immunoenzymatic Techniques, Elsevier Science Publishers, 1983) This method replaces the radioactive biological substance analogue with an enzyme labeled biological substance (hapten or antigen). Typical enzymes that can be used as labels in the enzyme immunoassay are listed in Table II.

TABLE II

Enzymes commonly used in enzyme immuno assay

Alkaline phosphatases
Glucose oxidases
Ureases
Peroxidases
β-Galactosidases
Glucose-6-phosphate dehydrogenases
Lysozymes
Malate dehydrogenases Such modified enzyme molecules retain their enzymatic activity and the enzyme-labeled biological substance will compete for antibody complex formation with the unknown amount of free biological substance in the system. The complexes may be separated in view of the insolubility in certain substances. The activity of the separated complex, or the part remaining in solution, is used as a measure of the amount of antigen originally present. The same principle may be applicable to a reverse system, using enzyme-labeled antibodies whenever the unmodified version of the same antibody present in biological fluids has to be determined.

There are several variations of the enzyme immuno assay. In one variation, known as enzyme-linked immunosorbent assay (ELISA), labeled and unlabeled antigen compete for attachment to a limited quantity of solid-phase antibody. The enzyme label that is displaced is measured, and the calculations that follow are essentially the same as in radioimmunoassay procedures.

The sandwich technique is another variation of enzyme immunoassay and relies on the multivalence of antigens and capacity to bind simultaneously with two molecules of antibody. The first antibody molecule is a solid phase reactant. It is used in excess to ensure binding of all the antigen molecules in the unknown sample. After that reaction is completed, an enzyme-labeled antibody is added and incubated with the complex resulting from the first phase. The labeled antibody then combines with available determinants on the antigen. Excess antibody is removed by washing and enzyme activity is then determined. As in other systems, the amount of enzyme bound to the complex is an indirect measure of the amount of antigen in the sample. Variations of this method include the second antibody method. In that method, antigen is reacted first with solid phase antibody and later with free antibody, neither of which is labeled. Then enzyme-labeled antibody with a specificity for the free antibody is used as the last reagent.

Most of the enzyme immunoassay techniques are classified as heterogeneous assays. This means that the bound labeled molecule must, at some point in the assay procedure, be separated from the free labeled molecule in order to perform the necessary calculations to determine the amount of unknown substance in the fluid. This requires a separation step in the assay and adds to both the time and expense of the assay procedure. There are enzyme immuno assay procedures that are homogeneous assays in that there is no separation of bound labeled substance and unbound labeled substance. Such a system does not require a solid phase reactant, but rather relies on an inhibition of enzyme activity by the combination of an antibody with an enzyme-labeled antigen or hapten. This type of assay is of limited usefulness since not all antigen-antibody combinations will result in a predictable diminution of enzyme activity.

Enzyme immunoassays are generally as sensitive as radioimmunoassays and are much safer because no radioactive isotopes are used. In addition, enzyme immunoassays generally require less sophisticated equipment than the radioimmunoassays. An enzyme immunoassay is generally much less expensive than a corresponding assay done by radioimmunoassay.

However, there are still significant problems associated with the typical enzyme immunoassay. The time required to run an enzyme immunoassay, for many applications, is too long. In most cases, an incubation period of at least several hours is required to perform the assay. In addition, the typical enzyme immunoassay comprises several washing steps and an additional incubation step with an enzyme substrate to develop a color which can be measured. The color from the enzyme reaction must then be measured in a spectrophotometer.

SUMMARY OF THE INVENTION

The solid phase diffusion assay of the present invention is not a heterogeneous assay and therefore does not require a separation step to separate bound labeled compounds from unbound labeled compounds. It is, on the other hand, not correct to call the solid phase diffusion assay of the present invention a classical homogeneous assay because there is no steric interaction between the binding molecule and the label. [In this assay, all of the labeled compound is bound to the adsorbent molecule in the solid phase]. The present invention is free of the problems associated with the aforementioned methods of detecting substances present in the biological fluids in minute concentrations. It provides a solid phase diffusion assay which can be performed in a relatively short period of time and is comparable in sensitivity to the radioimmunoassay. In addition, the solid phase diffusion assay of the present invention does not require any sophisticated measuring equipment. The solid phase diffusion assay of the present invention does not have to be performed in a laboratory and can be performed at a patient's bedside.

In accordance with the present invention, it has been determined that a wide variety of substances can be accurately and easily measured. These substances include any substance which is able to specifically interact with another substance. Such substances include immunogens, such as proteins, glycoproteins, nucleoproteins and large peptide hormones, such as insulin and growth hormone. These substances also include haptens such as drugs, vitamins, glycosides and polypeptides. Examples of other compounds which specifically interact with each other are lectins and sugars, enzymes and substrates, biotin and avidin, DNA and complementary DNA, RNA and complementary RNA, DNA and RNA and ligands and receptors for the ligands.

The principle of the solid phase diffusion assay is outlined in the following description using a competitive assay as an example. An adsorbent that is specific for a particular test substance is bound to an insoluble support such as nitrocellulose paper. A solution of an unknown concentration of the test substance to which the adsorbent is specific is mixed with a known concentration of enzyme-labeled test substance. A measured amount of the solution is applied to a single point on the insoluble support. The solution is allowed to diffuse in the insoluble support for several minutes. After diffusion is complete, the amount of diffusion is visualized by adding a substrate for the enzyme label. The diameter of the diffusion pattern on the solid support is proportional to the concentration of unlabeled test substance in the solution. The entire solid phase diffusion assay of the present invention takes only a few minutes to perform and the only measuring device required is a ruler.

Numerous variations of this assay using the described basic principle may be performed. The test may be performed as a sandwich assay. In this case, only the soluble test sample is applied onto the solid phase with the absorbent The solid phase is then incubated in a solution containing the labeled adsorbent and the binding of the labeled adsorbent is visualized after a washing step.

A preincubation step to label the test substance directly can be performed. In this case, the test substance and the labeled adsorbents are incubated together and the mixture is applied to the solid with the adsorbents.

The solid phase diffusion assay of the present invention can be used to monitor a product of another assay. In this application, the solid phase diffusion assay of the present invention is used as a visualization step for assays measuring different substances. For example, an immunoassay with liposomes containing enzymes can be performed in liquid phase. The supernate is then applied to the solid phase containing the adsorbents. The release of enzymes by the liposomes is measured after addition of the enzyme substrate solutions with detergent. The detergent is added to lyse the liposomes.

Another example of using the present invention as a visualization step for assays measuring different substances is the use of an antibody labeled with avidin/enzyme complex. This antibody/avidin/enzyme complex may be incubated with an unknown amount of antigen to which the antibody is specific. After the binding reaction is complete, the solution is applied to an insoluble support to which biotin is attached. The presence of antigen will cause the complexes to crosslink and reduce the number of free antibody avidin/enzyme complexes and, as a result, proportionally reduce the area of the diffusion pattern.

The label that is used in the solid phase diffusion assay of the present invention can be an enzyme, a radioactive isotope, a fluorescent compound, a dye, a substance which is visible under ultraviolet light or a carrier, such as a liposome, filled with one of the above labels. In addition, the label used in the solid phase diffusion assay of the present invention can also be one that can intrinsically be labeled. For example, protein can be visualized by adding a solution of the dye Coomassie Blue.

In the solid phase diffusion assay of the present invention, the maximum amount of solution required to determine the concentration of a particular test substance in the solution is between approximately one to 50 $\mu$l. Thus, for example, if a blood antibiotic level is required, a finger prick would supply enough blood to perform the assay. Conventional methods of measuring blood antibiotic levels require that several cubic centimeters of blood be drawn from a venous puncture.

Accordingly, it is an object of the present invention to provide a novel diffusion assay.

Another object of the present invention is to provide an assay that be performed by non-technical personnel.

Another object of the present invention is to provide an inexpensive assay for the measurement of trace amounts of substances.

Another object of the present invention is to provide a fast, one step assay for the measurement of trace amounts of substances.

Another object of the present invention is to provide a fast, inexpensive immunologic assay that can be supplied in kit form.

Another object of the present invention is to provide a qualitative and quantitative assay, that requires as a measuring instrument only a ruler.

Another object of the present invention is to provide a versatile assay that can be used to measure the concentration of a wide variety of substances.

Another object of the present invention is to provide a visualization step for other types of assays.

Yet another object of the present invention is to provide a method of assaying plasma concentrations of substances without prior separation of the plasma from the whole blood.

A further object of the present invention is to provide a method of assaying low concentrations of substances in a small volume of solution.

These and other objects, features and advantages of the present invention will become apparent after a review of the following detailed description of the disclosed embodiment and the appended drawing and claims.

DETAILED DESCRIPTION OF THE PREFERRED EMBODIMENT

The solid phase diffusion assay of the present invention is an assay for the quantitative and/or qualitative measurement and detection of very small concentrations of a wide range of soluble substances. In the solid phase diffusion assay of the present invention, an adsorbent that is specific for a particular test substance is bound, either covalently or noncovalently, to a support that is insoluble in the assay solvent The following description applies to the competitive variant of the test. A solution of an unknown concentration of a test substance is prepared. To that solution is added a known amount of labeled test substance. A small volume of the solution containing the test substance and labeled test substance is applied to an single point on an insoluble, adsorbent treated support. As the test substance and the labeled test compound diffuse through the support, they compete for binding sites on the adsorbent treated insoluble support. The circular area covered by the labeled compound increases with displacement by the test sample.

As used herein, the term "ligand" describes any compound for which a receptor naturally exists or can be prepared. The term "receptor" is used for any compound or composition capable of recognizing a particular spatial or polar organization of a molecule, i.e., epitopic site. illustrative receptors include, but are not limited to, naturally occurring receptors, e.g., thyroxin binding globulin which will specifically bind thyroxin; Staphylococcal protein A which specifically binds immunoglobulins; antibodies; enzymes which specifically bind substrates; Fab fragments; lectins and the like.

Figure 1A:
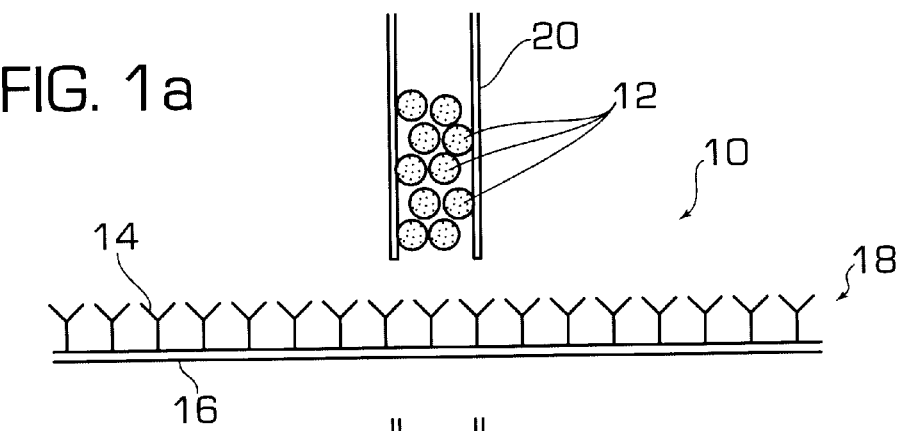
FIGS. 1(a)–1(c) are schematic views of the solid phase diffusion assay of the present invention using only labeled test molecules
Figure 1B:
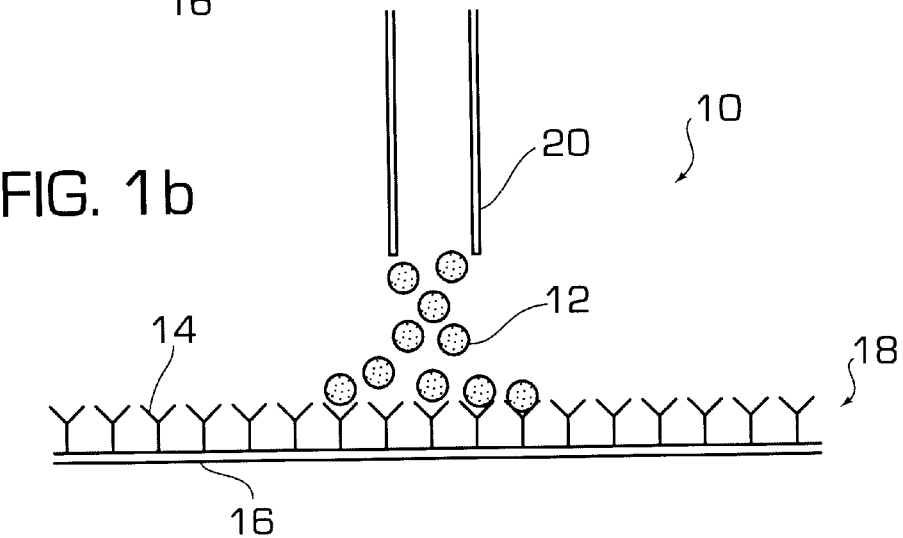
Figure 1C:
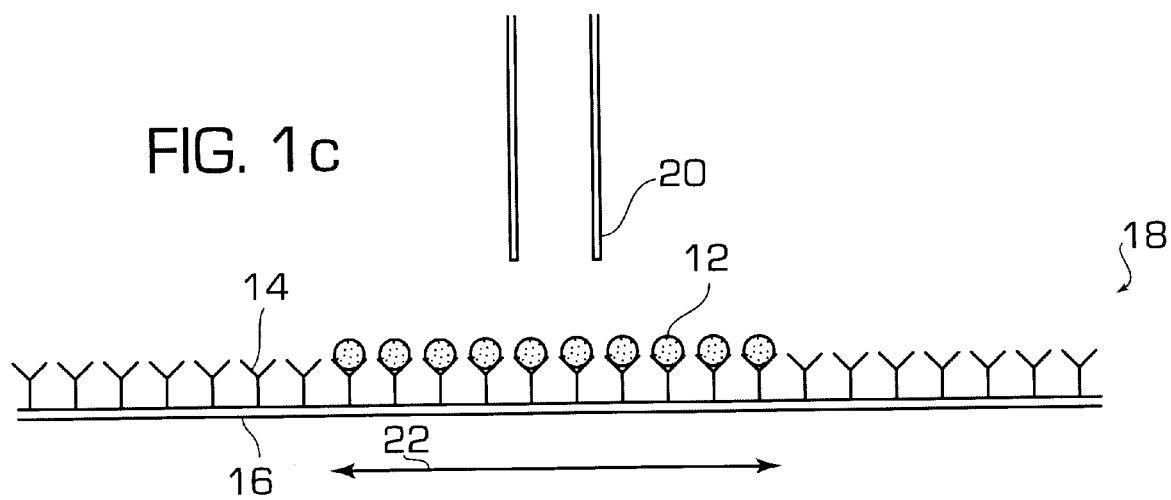

Referring now to the drawings in which like numbers indicate like elements throughout the several views, it will be seen that there is disclosed in FIGS. 1(a)–1(c) and FIGS. 2(a)–2(c) the solid phase diffusion assay of the present invention. FIGS. 1(a)–1(c) the binding of an unknown concentration of labeled test substance molecules. This figure shows the use of the solid phase diffusion assay 10 of the present invention as a measurement step of a conventional assay. Shaded spheres represent labeled test substance molecules 12 in solution. These molecules may either be ligands, such as immunogens or haptens, or they may be receptors specific for the ligand. Examples of receptors are antibodies. Adsorbent molecules 14 can likewise be either antigens or receptors. The adsorbent molecules that are specific for the test substance molecules 12 are bound to a support 16 that is insoluble in the solvents that are used in the particular test. One example of an insoluble support is nitrocellulose paper. The insoluble support 16 is treated with the adsorbent molecules 14. For example, a typical adsorbent molecule that can be used in the present invention are antibodies that are specific for a particular antigen or hapten. The antibody molecule has an overall positive charge. The nitrocellulose paper has an overall negative charge. When the antibody molecules are applied in solution to the nitrocellulose paper, the positively-charged antibodies are jonically bound to the negatively-charged nitrate groups on the nitrocellulose paper. It is to be understood that other solid supports may be used and that the adsorbent molecules may be bound to the solid support either ionically or covalently. The adsorbent molecules 14 therefore provide specific binding sites on the support 16 to which the test substance molecules 12 can be bound The insoluble support 16 treated with the adsorbent molecules 14 provides the solid phase 18 of the assay.

A known amount of test substance molecules 12 is applied to the solid phase 18 by a capillary tube 20 or by other well known devices such as a micropipet or a microbiological loop. As shown in FIG. 1(b), when the test substance molecules 12 are applied to the solid phase 18, they diffuse radially outward from the point of application through the solid phase. As the test substance molecules 12 diffuse through the solid phase 18, the test substance molecules bind to the free adsorbent molecules 16 sites.

As shown in FIG. 1(c), when all of the labeled test substance molecules 12 become bound to adsorbent molecules 14, diffusion of the test substance molecules through the solid phase 18 stops. The bound test substance molecules 12 provide a circular diffusion pattern on the solid phase. The circular diffusion pattern has a diameter such as at 22, which can be measured by well known techniques which will vary depending on the type of labeled substance used. The diameter of the diffusion pattern, will be proportional to the amount of labeled test substance in solution.

Figure 2A:
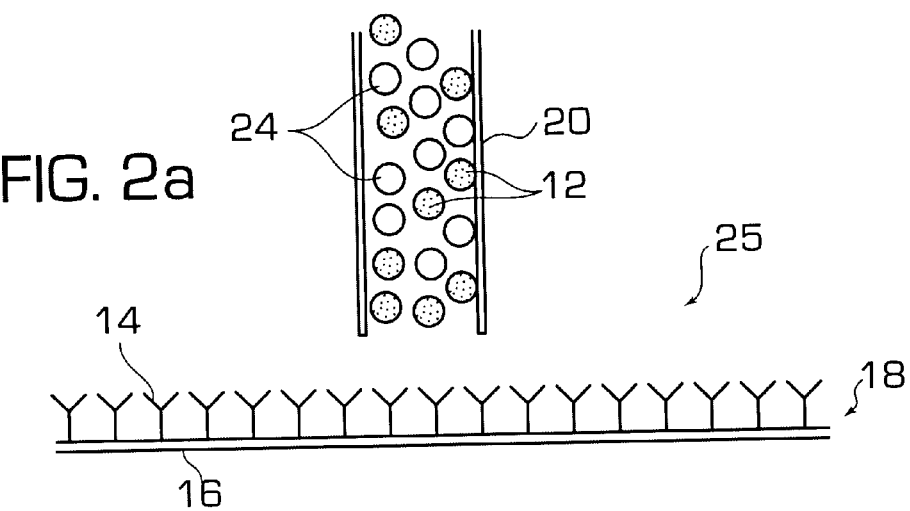
FIGS. 2(a)–2(c) are schematic views of a solid phase diffusion assay with labeled test molecules and unlabeled test molecules.
Figure 2B:
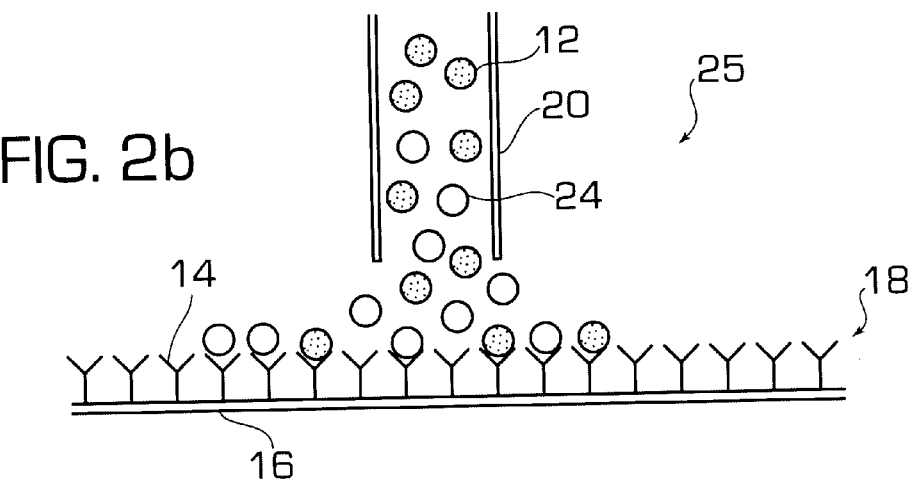
Figure 2C:
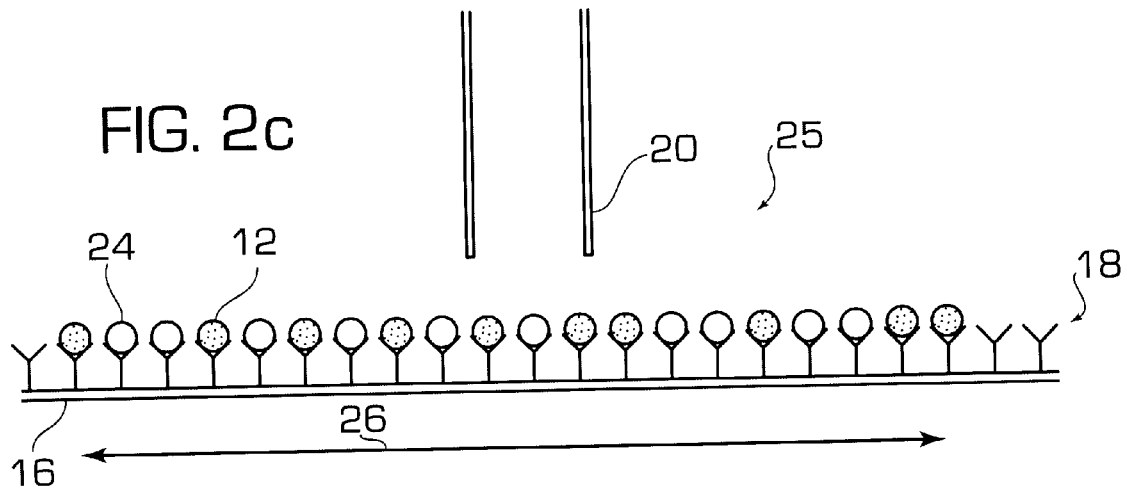

Referring now to FIGS. 2(a)–2(c), there is shown the solid phase diffusion assay 25 of the present invention with an unknown amount of Unlabeled test substance added to the solution of known labeled test substance. This variant of the solid phase diffusion assay utilizes the principle of competition between the labeled test substance and the unlabeled test substance for binding sites on the solid phase. An unknown concentration of unlabeled test substance molecules 24, such as an antigen or a hapten, is mixed with a known concentration of labeled test substance molecules 14 to provide a test solution. The solid phase 18 is prepared as described above; however, the adsorbent molecules 14 are selected such that they will provide binding sites for both the labeled test substance molecules 14 and the unlabeled test substance molecules 24.

The test solution is applied to the solid phase 18 in the manner described above. The test solution diffuses radially outwardly from the point of application through the solid phase 18. Both the labeled test substance molecules 12 and the unlabeled test substance molecules 24 compete for binding with the free adsorbent molecules 14 binding sites. Diffusion of the test solution through the solid phase 18 continues until all of the labeled test substance molecules 12 and all of the unlabeled test substance molecules 24 are bound to the adsorbent molecules 14.

Because some of the binding sites are occupied by unlabeled test substance molecules 24, the labeled test substance molecules 12 will diffuse outwardly farther from the point of application than if no unlabeled test substance molecules were present. As a result, the diffusion pattern of the test solution has a diameter 26, FIG. 2(c) which is greater than the diameter 22, FIG. 1(c), of the diffusion pattern for the labeled test substance molecules 12 alone.

The distance that the labeled test substance travels is greater in FIG. 2c than in FIG. 1c because, in FIG. 2c, a percentage of the adsorbent binding sites are occupied by unlabeled test substance allowing the labeled test substance to diffuse farther before encountering a free adsorbent binding site. Thus, the diameter of the diffusion pattern formed by the labeled test substance is proportional to the concentration of unlabeled test substance in the solution.

There are many variations of the solid phase diffusion assay of the present invention. For example, there are situations where the test substance either (a) cannot be labeled, or (b) where the affinity between the test substance and the receptors is too low to be used in the solid phase diffusion assay of the present invention or (c) where a very high sensitivity is desired or (d) where one may wish to use the same solid phase diffusion reagents to measure the concentration of different substances.

In the above situations, a preliminary step is required to measure the above test substances. In case (a) where the test substance cannot be labeled, the receptor for the test substance can be labeled and this receptor is then assayed in a final step of the solid phase diffusion assay of the present invention.

If the affinity between the test substance and the receptor is low, the test substance or the receptor can be conjugated with a high affinity ligand or receptor such as the biotin-(ligand)-avidin(receptor) system. The solid phase diffusion assay of the present invention may then be performed using the high affinity ligand and receptor. (An example is described below.)

The sensitivity of the solid phase diffusion assay of the present invention can be greatly increased by employing an amplification step. An example of this step is using a complement system or by incorporating antibodies against the test substance into the membrane of a unilamellar liposome which is filled with an enzyme or other label.

Use of the same solid phase diffusion assay of the present invention for different test samples may be performed by linking biotin to the insoluble support and using avidin as a ligand to measure different test substances. In this case, the enzyme-labeled avidin is conjugated to antibodies against the different test samples. The test sample is then incubated with its complementary- labeled antibody and the antibody assay in the biotin/avidin solid phase diffusion assay. Presence of the antigen diminishes the amount of labeled antibodies by crosslining which will cause a diminution of the area of the diffusion pattern on the insoluble support.

The test solution in the solid phase diffusion assay of the present invention can be applied in several ways. The test solution can be applied to a single point directly onto the treated insoluble support by a capillary tube, a micropipet or by a microbiological loop. In addition, a sheet of plastic or tape with a small hole can be placed on the insoluble support. The test solution can then be applied directly onto the plastic sheet or tape directly over the hole. The test solution will then diffuse through the hole and into the insoluble support. The test solution can also be applied by allowing one end of a strip of treated insoluble support to come into contact with a measured amount of test solution. The solution is then allowed to diffuse into the insoluble support. The distance the labeled test substance diffuses is proportional to the amount of unlabeled test substance in the solution.

It will be understood that the label conjugated to the test substance can be an enzyme. The enzyme-labeled test substance is visualized by adding the enzyme substrate and briefly incubating the solid support until enough color appears so that the diffusion pattern can be measured. The test procedure can also be simplified by adding one component of the enzyme substrate solution to the test sample mixture and incorporating the second component into the solid phase. By applying the sample mixture, the enzyme substrate is automatically reconstituted.

The label conjugated to the test substance can also be a radioactive isotope. If the label is a radioactive isotope, the diffusion pattern of the test substance solution is visualized by placing the insoluble support in contact with a sheet of X-ray film and exposing the film for a period of time sufficient to register the diffusion pattern on the film. This time is dependent upon the isotope that is used and the specific activity of the isotope. After exposing the film to the support, the film is developed and the diameter of the diffusion pattern is measured.

The label conjugated to the test substance can also be a fluorometric compound. If the label is a fluorometric compound, the diffusion pattern of the test substance solution on the insoluble support is visualized by placing the support under an ultraviolet light. The ultraviolet light will cause the compound that is linked to the test substance to fluoresce and the diameter of the diffusion pattern can be measured with a ruler.

The label conjugated to the test substance can also be a dye, such as colloidal gold, colloidal silver, (Janssen Pharmaceutical, Beerse, Belgium) Congo red 22120, 4'6'-diamidino- 2-phenylindole, eosin 10B and hematoxylin 75290. (Sigma Chemical Company, St. Louis, Mo.).

A label conjugated to a test substance may be detected by one of the detection methods widely used for conventional thin layer chromatography. This includes dyes which have an affinity for certain chemicals. (See *Visualization Procedures in the Practice of Thin Layer Chromatography*, J C Touchstone and M. F. Dobbins, pgs. 161–219, 1970).

The label conjugated to the test substance can also be indirectly linked to the test substance. For example, if the test substance is a hapten, it is possible to bind a protein to the hapten and then to conjugate the label to this protein. Alternatively, an antibody against the antigen can be labeled and used as the labeled antibody-antigen complex in the assay.

The label conjugated to the antigen can also be incorporated into a carrier such as a liposome. (See *Journal of Immunological Methods*, 62:155–162, 1983). In this procedure, the antigen is integrated into the membrane of the unilamellar liposome. The enzyme is located in the interior of the liposome. After the test substance with the liposome label has diffused in the solid support, a detergent, with the enzyme substrate, is added to the solid support. The detergent will disrupt the liposome membrane allowing the now exposed enzyme to react with the enzyme substrate. Antibodies against the enzyme or dye that are held inside of the liposome can be incorporated in the solid phase to prevent non-specific diffusion of the label.

The different characteristics of the solid support strongly influence the performance of the assay. It is therefore possible to develop solid supports specially suited for particular needs of the solid phase diffusion assay of the present invention. As a general rule, the thickness of the solid support is indirectly proportional to the amount of sample needed to cover a given surface and to the discriminatory capacity of the assay. The concentration of hydrophilic and hydrophobic components also influences the diffusion behavior of the sample. The binding capacity of the solid support for the receptor is important to the sensitivity of the solid phase diffusion assay of the present invention. Methods for preparations of various solid supports are well known to one skilled in the art.

The solid phase insoluble supports useful in the present invention can be any support that has an overall negative charge so that an adsorbent molecule (either a receptor or a ligand) with an overall positive charge can bind non-covalently to the the insoluble support. Examples of these types of supports are nitrocellulose paper, blotting membranes, diethylaminoethyl ion exchange paper and blot adsorbent filter papers. The solid phase insoluble supports can also be any support that has a functional group attached to the support to which an adsorbent molecule (either a receptor or a ligand) can be covalently attached. Examples of these types of supports are aminobenzyl-oxymethyl (ABM) paper, 2-aminophenylthioether (APT) paper, cyanogen. bromide activated paper (CBA) (See *Methods in Enzymology*, R. Wu (ed.) 1979, Academic Press New York, 68:436–442 for a discussion of CBA paper), diazobenzyloxymethyl cellulose paper (DBM), diazophenylthioether cellulose paper (DPT) and nitrobenzyloxymethyl cellulose paper (NBM).

Methods that can be used to couple chemicals to the solid phase support depend, in part, on the chemical composition of the support and the chemical composition of the chemical to be coupled to the support. Chemicals can be coupled to a support by use of cyanogen bromide coupling, silation, diazo coupling, carbodiimides coupling, glutaraldehyde coupling and the use of heterobifunctional reagents. In many cases, due to stereochemical inhibition, spacer groups are required to couple one chemical to another chemical. Common spacer groups include, but are not limited to, diamino alkyl or aryl groups, aryl carboxyclicic acid or gamma amino alkyl groups, thiol, hydroxyl and mercurated bases.

The exclusion limit dictated by the pore size of the insoluble support will determine the size of the particle that can diffuse in the solid phase. The pore size of the solid phase can be utilized to eliminate a separation step in an assay. For example, when heparinized blood is analyzed, the cellular components of the blood must usually be separated from the fluid or plasma portion of the blood before any analysis can be performed. This is usually done by centrifugation. With the solid phase diffusion assay of the present invention, this centrifugation step can be eliminated because the pore size of the insoluble support can be selected to block the diffusion of the cellular components of the blood.

In a further variation of this embodiment of the solid phase diffusion assay of the present invention, the test solution may be applied to the insoluble support through a filter. The test solution is applied to the top of the filter and the test solution diffuses through the filter and into the insoluble support. Examples of typical filters include, but are not limited to, blotting paper and diethylaminoethyl ion exchange paper. An example of using this procedure is in separating blood cells from plasma where the insoluble support would lyse the erythrocytes in whole, heparinized blood. The released hemoglobin from the lysed cells would cause a high background color in the insoluble support and make the visualization of the diffusion pattern difficult.

The application of test sample to the insoluble support can be modified in the following manner. A tiny plastic sheet or piece of plastic tape can be prepared with a hole punched in the center of the sheet or tape. The diameter of the hole can be between approximately 1 to 5 mm. The plastic sheet or tape is then placed on the insoluble support. The test sample may then be rapidly applied to the insoluble support over the hole in the sheet or tape. The test sample will then diffuse through the hole into the insoluble support The unlabeled test substances that can be assayed by the solid phase diffusion assay of the present invention include, but are not limited to, the class of substances known as antigens. Antigens can be broken down into two groups: immunogens and haptens.

Immunogens are compounds which, when introduced into a chordate, will result in the formation of antibodies. Representative of the immunogens are proteins, glycoproteins and nucleoproteins, such as peptide hormones, serum proteins, complement proteins, coagulation factors, and viral or bacterial products. Certain body compounds with ubiquitous presence in all animal species cannot be used to produce antibodies because these compounds are not recognized as foreign by the immunized animal. These compounds can be rendered "foreign" by chemical derivation. The test substance in an assay has to undergo the same derivation procedure if antibodies against an altered compound are used.

Table III is a partial list of some of the types of immunogens that can be quantitated by the solid phase diffusion assay of the present invention.

TABLE III

| proteins | glycoproteins |
| nucleoproteins | peptide hormones |
| serum proteins | complement proteins |
| coagulation factors | microbiocidal products |
| viral products | bacterial products |
| fungal products | specific Immunogens |
| albumin | angiotensin |
| bradykinin | calcitonin |
| carcinoembryonic antigen | chloriomamotropin |
| chorogonadotropin | corticotropin |
| erythropoietin | Factor VIII |
| fibrinogen | alpha-2-H globulin |
| follitropin | Gastrin |
| gastrin sulfate | glucagon |
| gonadotropin | haptoglobin |
| Hepatitis B surface antigen | immunoglobulins (A,D,E,G,M) |
| insulin | lipotropin |
| kallidin | lipotropin |
| melanotropin | oxytocin |
| pancreozymin | placental lactogen |
| prathryin | proangiotensin |
| prolactin | somatotropin |
| relaxin | secretin |
| somatomadin | somatostatin |
| thryrotropin | vasotocin |
| thymopoietin | vasopressin |
| alpha-1-fetoprotein | alpha-2-H globulin |

Haptens are compounds which, when bound to an immunogenic carrier and introduced into a chordate, will elicit formation of antibodies specific for the hapten. Representative of the haptens are steroids such as estrogens and cortisones, low molecular weight peptides, other low molecular weight biological compounds, drugs such as antibiotics and chemotherapeutic compounds, industrial pollutants, flavoring agents, food additives, and food contaminants, and/or their metabolites or derivatives.

The above classes are obviously incomplete in that the solid phase diffusion assay of the present invention can be used to assay for any molecule to which an antibody can be formed. In addition, the solid phase diffusion assay of the present invention can be used to identify and quantitate an antibody molecule.

An antibody that can be used in the solid phase diffusion assay of the present invention can be produced by introducing the antigen to be assayed, if it is an immunogen, into a living chordate. The antibodies, which are produced in response to the introduction of the immunogen, are proteins that coat the immunogen and detoxify it, precipitate it from solution, or simply bind to it. The antibody protein forms a receptor which is geometrically arranged so that the immunogen fits the spatial arrangement of the protein. In the case of a hasten, an extra step is involved in preparing the antibody. The hapten must be conjugated to an immunogenic carrier prior to introduction into a living vertebrate. The method of preparing the antibodies from haptens is well known to those skilled in the art.

Another source of antibodies that can be used in the solid phase diffusion assay of the present invention is monoclonal antibodies. The technique for producing monoclonal antibodies involves the fusing of spleen lymphocytes with malignant cells of bone marrow primary tumors. The method creates a hybrid cell line, arising from a single fused cell hybrid, or clone, which possesses characteristics of both the lymphocytes and myeloma cell lines. Like the lymphocytes (taken from animals primed with the particular antigen), the fused hybrids, called hybridomas, secrete a single type of immunoglobulin specific to the antigen; moreover, like the myeloma cell lines, the hybrid cell line is immortal. The combination of these two features has had a major impact in fields of research and medicine in which conventional antisera are used. Whereas antisera derived from vaccinated animals are variable mixtures of antibodies which never can be reproduced identically, monoclonal antibodies are highly specific immunoglobulins of a single type. The single type of immunoglobulin secreted by a hybridoma is specific to one and only one antigenic determinant on the antigen, a complex molecule having a multiplicity of antigenic determinants. (See C. Milstein, *Scientific American*. 243(4):66–74, 1980).

The antigen-enzyme immunocomplex (or antibody-enzyme complex) serves as the labeling agent The preparation and use of soluble antigen or antibody enzyme complexes has been described by Stemberger et al., in *J. Histochrem, Cytochem.* 18:315 (1970). The desirable enzymes will be those having a high turnover rate, which can be readily conjugated to a wide variety of ligands, which will be relatively insensitive to nonspecific interactions, will have a turnover rate subject to modulation by a macromolecular reagent and will produce a product which is visible, particularly by absorption of emission of electromagnetic radiation. The enzyme that is preferred for use in the solid phase diffusion assay of the present invention is horseradish peroxidase (Sigma Chemical Company, St. Louis, Mo.) The preferred enzyme can be easily complexed to a wide variety of compounds. Other enzymes that can be used as labels are alkaline phosphatase, glucose oxidase, peroxidase, β-galactosidase, urease, glucose-6-phosphate dehydrogenase, urease, lysozyme and malate dehydrogenase.

Any system where there is a specific interaction among substances can be used in the solid phase diffusion assay of the present invention. Examples of systems other than the antibody/antigen systems which are useful in the present invention include lectins/sugar systems, enzyme/substrate, hybridization of DNA and RNA molecules, the biotin/avidin system and Staphylococcal protein A/immunoglobulin system.

As a matter of convenience, the reagents for the solid phase diffusion assay can be provided as kits, where the reagents are in predetermined ratios, so as to substantially optimize the sensitivity of the assay in the range of interest. After reconstitution of dry reagents, in predetermined volumes, the concentration of the reagents will be at appropriate levels.

The present invention is illustrated further by the following examples which are not to be construed as limiting the invention to the specific procedures described in them.

EXAMPLE I

The following example demonstrates the solid phase diffusion assay of the present invention as used to detect small quantities of inactivated horse radish peroxidase. This is an example of a competitive assay based on an antibody/antigen interaction where the competitive compound by itself is used as the label. Anti-peroxidase antibodies are bound to the solid-phase which, in this example, is nitrocellulose paper. Inactivated horseradish peroxidase is the antigen and active peroxidase corresponds to the labeled antigen in this assay.

Figure 3:
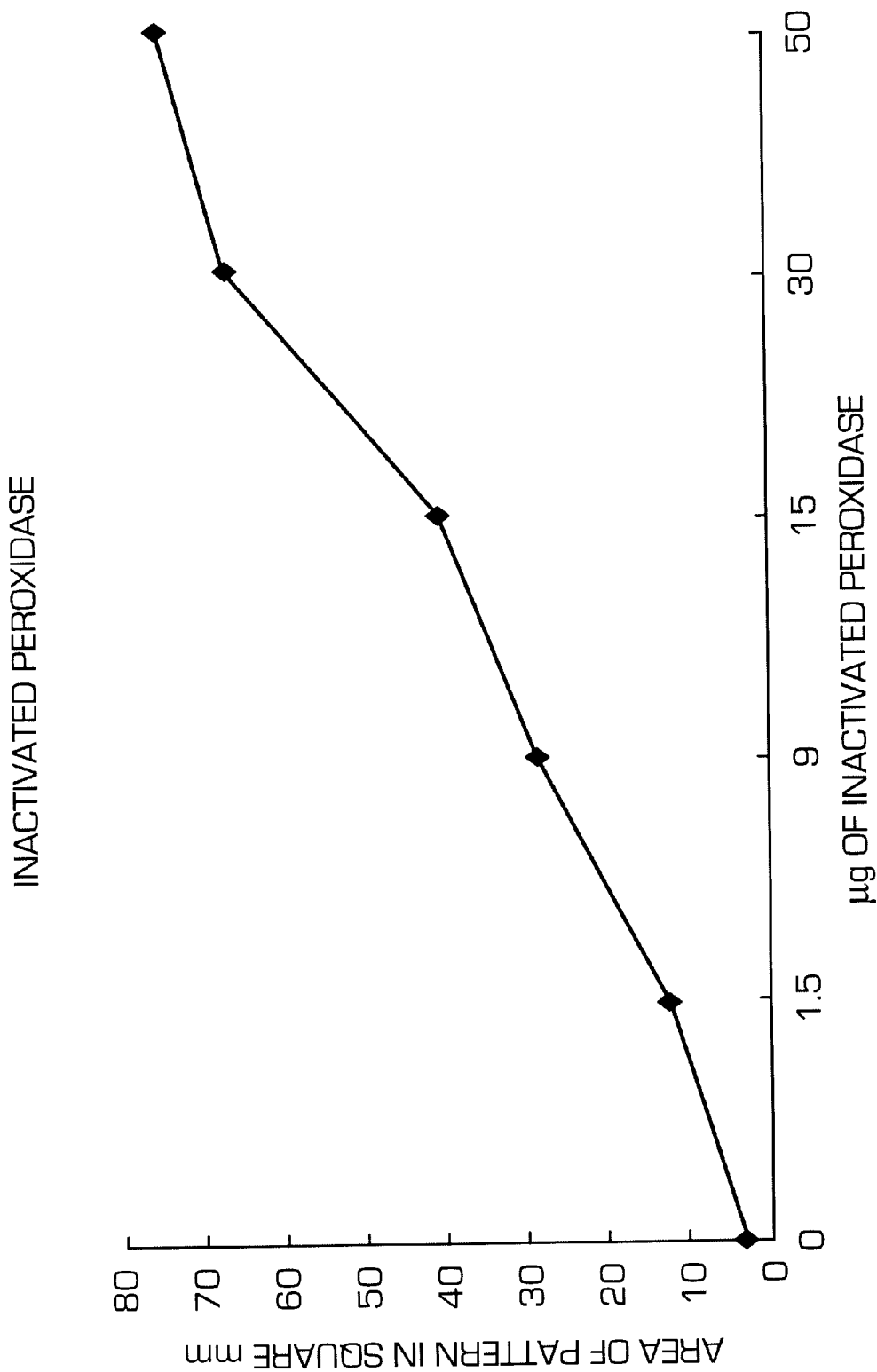
FIG. 3 is a standard curve measuring inactivated peroxidase by the solid phase diffusion assay of the present invention.

A standard curve is prepared by preparing a concentrated solution of inactivated horseradish peroxidase. The concentration of active peroxidase (the label in this case) was determined as follows. Several dilutions of a solution with 1 mg/ml of peroxidase were mixed with ten percent rabbit serum and phosphate buffered saline (no test solution) and were applied to the treated nitrocellulose. The highest dilution that still provides a measurable diffusion patter was used as the label in this example. The solution of inactivated horseradish peroxidase (fifty $\mu$g/ml) is serially diluted in phosphate buffered saline containing ten percent rabbit serumn 2 ½ $\mu$l of each of the solutions of inactivated horseradish peroxidase is mixed with 2 ½ $\mu$l of a solution containing 0.3 $\mu$g of the active peroxidase (the labeled antigen in this example). The 5 $\mu$l of solution is then carefully applied by diffusion from a capillary tube to the nitrocellulose papers containing the bound anti-peroxidase antibodies. The solution diffuses from the capillary tube into the nitrocellulose paper and forms a circular diffusion pattern. The nitrocellulose papers are then immersed in a solution of horseradish peroxidase substrate (4-chloro-1-naphthol and hydrogen peroxide) and incubated until a blue circle developed. As shown in FIG. 3, the area of the circular diffusion pattern is proportional to the amount of Unlabeled antigen in the solution. In accordance with the present invention, it has been found that only a single standard curve has to be run for a given set of antibody and labeled antigen reagents. The detailed embodiment of the the solid phase diffusion assay of the present invention are as follows:

The nitrocellulose paper (Bio-Rad, Rockville Centre, N.Y., No. 162–0115, 0.45 microns) is cut into pieces with a dimension of approximately 1 square incn. These pieces are then washed for 10 minutes in phosphate buffered saline (pH 7.2). The washed papers are then incubated at 4° C. for 12 hours in a solution containing 10 mg/ml rabbit anti-peroxidase immunoglobulin G (Batch C1, affinty chromatography purified). After the 12 hour incubation, the papers are again washed for 10 minutes in phosphate buffered saline. The papers are then incubated for 2 hours in a solution of 5% serum albumin. This step is performed to saturate all non-specific binding sites. The papers are again washed in phosphate buffered saline. After a short wash in distilled water, the membrane pieces are air dried and stored at room temperature in a humid chamber.

The antigen that is used in this example was inactivated horseradish peroxidase. This antigen is prepared by dissolving 1.5 mg horseradish peroxidase (Type VI, Sigma Chemical Company,. St. Louis, Mo., No. P-8375, Lot 43F-9589) in phosphate buffered saline. The enzyme is inactivated by adding hydrogen peroxide to a final concentration of 1.0% and then dialyzed against phosphate buffered saline overnight.

2.5 $\mu$l of the sample containing the unknown horseradish peroxidase antigen is mixed with 2.5 $\mu$l of a solution containing 0.3 $\mu$g of activated peroxidase. The 5 $\mu$l solution is carefully applied to an antibody-treated nitrocellulose paper by diffusion from a capillary pipet. The substrate solution is made up as-follows: 15 mg of 4-chloro-1-naphthol (Bio-Rad, Rockville Centre, N.Y., No. 170-6534) is dissolved in 5 ml of methanol. To this solution is added 25 ml of distilled water and 15 $\mu$l of methanol. To this solution is added 25 ml of distilled water and 15 $\mu$l of 30% hydrogen peroxide. A blue circular pattern develops after several minutes.

To determine the concentration of antigen in the test solution, the area of the circular pattern is measured. By using the standard curve, an accurate value for the concentration of antigen in the solution can be determined.

FIG. 3 shows the relationship between the area of the diffusion pattern and the concentration of unlabeled, inactivated peroxidase in the test samples.

EXAMPLE II

This Example demonstrates the solid phase diffusion assay of the present invention as used to detect low concentrations of the antibiotic gentamicin in solution. This is an example of a competitive assay based on an antigen/antibody interaction where the test substance is a hapten and the labeled compound comprises a hapten bound to a carrier to which the label is bound.

The nitrocellulose paper (Bio-Rad, Rockville Centre, N.Y., No. 162-0115, 0.45 microns) is cut into pieces with a dimension of approximately 1 square inch. These pieces are than washed for 10 minutes in phosphate buffered saline (pH 7.2). The washed papers are then incubated at 4° C. for 12 hours in whole goat serum containing goat anti-gentamicin antibodies diluted 1:3 in phosphate buffered saline. No saturation step is required in this Example due to the high protein concentration of the diluted goat serum. The papers are then washed in phosphate buffered saline. After a short wash in distilled waters the membrane pieces are air dried.

The gentamicin is chemically linked to bovine orosomucoid using the carbodiimide coupling procedure which is well known to those skilled in the art. After the gentamicin is linked to the orosomucoid, horseradish peroxidase is then linked to the orosomucoid protein using the glutaraldehyde method (See S. Avrameas, *Immunochemistry*, Vol.1 6:43, 1969). This procedure produces a complex made up of orosomucoid-gentanmicin- horseradish peroxidase complex.

The orosomucoid-gentamicin-horseradish peroxidase complex is purified using the procedure of affinity chromatography. One gram of cyanogen bromide activated chromatography agar gel, sold under the trademark "SEPHAROSE 4B" (Pharinacia Fine Chemicals, Upsula, Sweden) is washed in 1 mMHCl. 10 mg/ml of the gentamicin- orosomucoid-horseradish peroxidase is then covalently coupled to the SEPHAROSE 4B using the manufacturers standard protocol. The resulting gel is then poured into a small chromatography column (Economo column, Bio-Rad). The goat anti-gentamicin antibodies are then adsorbed onto the column by passing 5 ml of the goat anti-gentamicin serum diluted 1 to 10 in phosphate buffered saline through the column. The antibody is next covalently linked to the solid phase by incubation with a 0.02M glutaraldehyde solution during 2 hours at room temperature. Free binding sites of the glutaraldehyde are saturated with glycine buffer and the column is then extensively washed with phosphate buffered saline.

The affinity column is then used for purification of the gentamicin-orosomucoid-peroxidase complex. 0.1M HCl and 0.2M glycine at a pH of 2.5 is used for elution of the labeled complex. The pH of the eluate is immediately corrected by adding solid Tris (Tris(hydroxymethyl)-aminomethane, Sigma Chemical Company, St. Louis). The resulting solution of purified gentamicin-orosomucoid- peroxidase complex is then dialyzed against phosphate buffered saline before storage.

The solutions for determining the standard curve are prepared in phosphate buffered saline, 10% normal rabbit serum, containing 6 different gentamicin dilutions. The concentrations of gentanmicin in the standard curve range between 0.4 $\mu$g/ml to 12.4 $\mu$g/ml. The protein concentration of the labeled gentamicin-orosomucoid-peroxidase complex is approximately 0.3 mg as determined by the absorbence of the solution at 280 nm. 5 $\mu$l of each dilution is applied with a capillary tube onto the nitrocellulose paper. After the test fluid diffuses into the nitrocellulose paper is then submerged in a substrate. solution. The substrate solution is made up as follows: 15 $\mu$g of 4-chloro-1-naphthol (Bio-Rad, Rockville Centre, N.Y., No. 170-6534) is dissolved in 5 ml of methanol. To this solution was added 25 ml of distilled water and 15 $\mu$l of 30% hydrogen peroxide. A blue circular pattern develops after several minutes.

Figure 4:
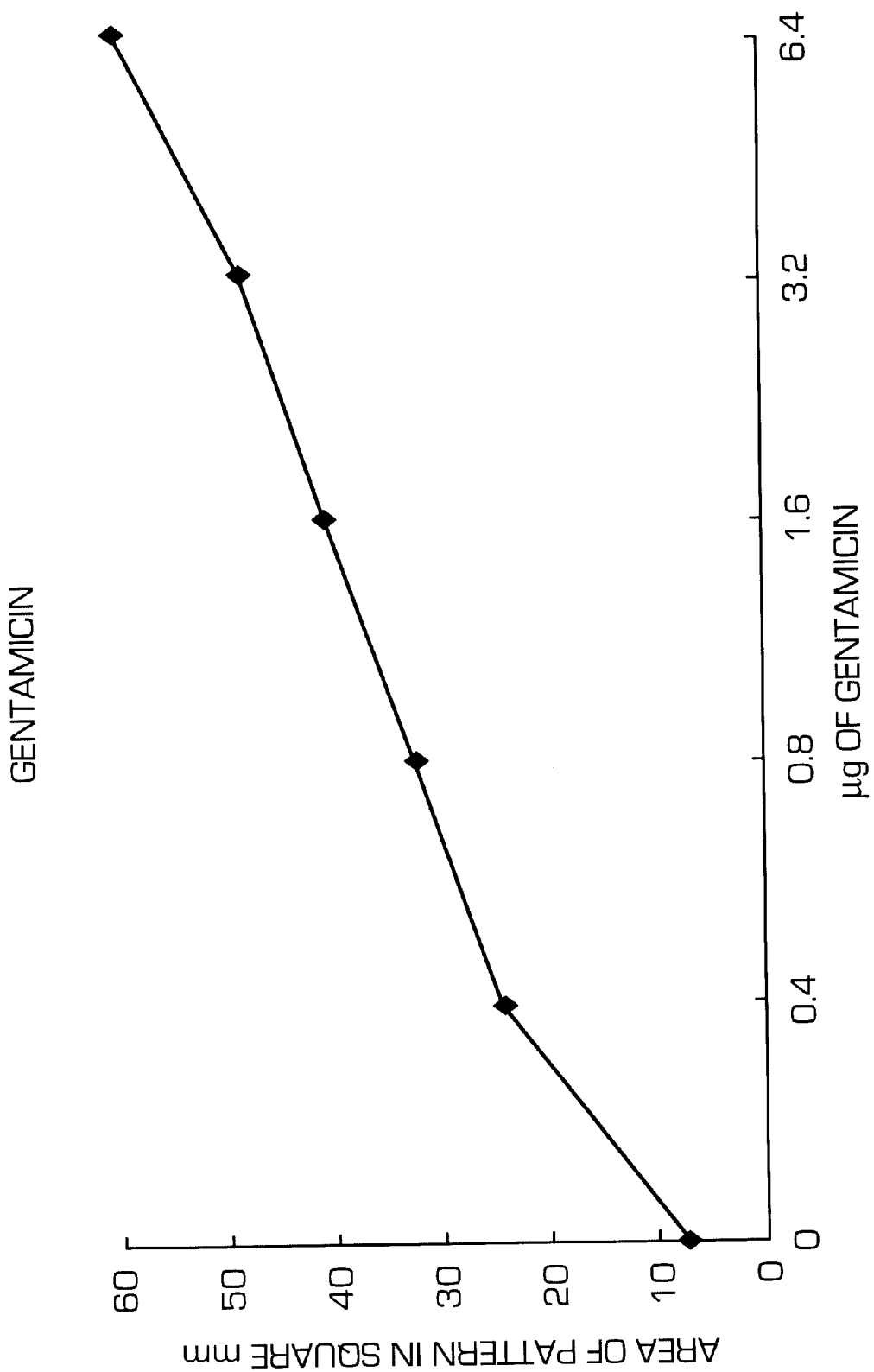
FIG. 4 is a standard curve measuring gentamicin by the solid phase diffusion assay of the present invention.

FIG. 4 shows the relationship between the area of the diffusion pattern and the concentration of unlabeled, gentamicin in the test samples.

EXAMPLE III

The following example demonstrates the solid phase diffusion assay of the present invention as used to detect low concentrations of the drug Theophylline. This is another example of an antigen-antibody interaction where the test substance is a low molecular weight hapten and the labeled compound comprises a hapten bound to horseradish peroxidase. This test also uses a monoclonal antibody as opposed to a heterogeneous antibody.

The nitrocellulose paper (Bio-Rad, Rockville Centre, N.Y., No 162-0115, 0.45 microns) is prepared as described in Examples 1 and 2. The washed papers are then incubated in phosphate buffered saline containing a mixture of 10 $\mu$g/ml of mouse monoclonal antibody against Theophylline and 2 mg of bovine serum albumin (Sigma Chemical Company, St. Louis) overnight at 4° C. The papers are then washed in phosphate buffered saline, air dried and stored in a humid chamber.

The Theophylline is conjugated to horse radish peroxidase. (See theophylline radioimmunoassay: Synthesis of Antigen and Characterization of Antiserum, C. E. Coole, et.al., *Research Communications in Chemical Pathology and Pharmacology*. Vol 13, No. 3, 1976.) The Theophylline/horse radish peroxidase conjugate is purified using affinity chromatography by the same procedure as described in Example 2 using the monoclonal anti-Theophylline antibody.

A standard curve is prepared containing six-different Theophylline dilutions in phosphate buffered saline and 10% rabbit serum. The concentrations of Theophylline range between 1.6 and 25.6 μg/ml. A mixture containing 2 ½ μl of a 1 to 2 dilution of the labeled antigen in 10% rabbit serum and 2 ½ μl of each dilution is applied with a capillary tube onto the nitrocellulose paper. After diffusion of the fluid into the nitrocellulose paper, the paper is submerged into the above described substrate solution and the color reaction allowed to develop. The diameters of the diffusion patterns are then measured and the area of the diffusion pattern is calculated.

Figure 5:
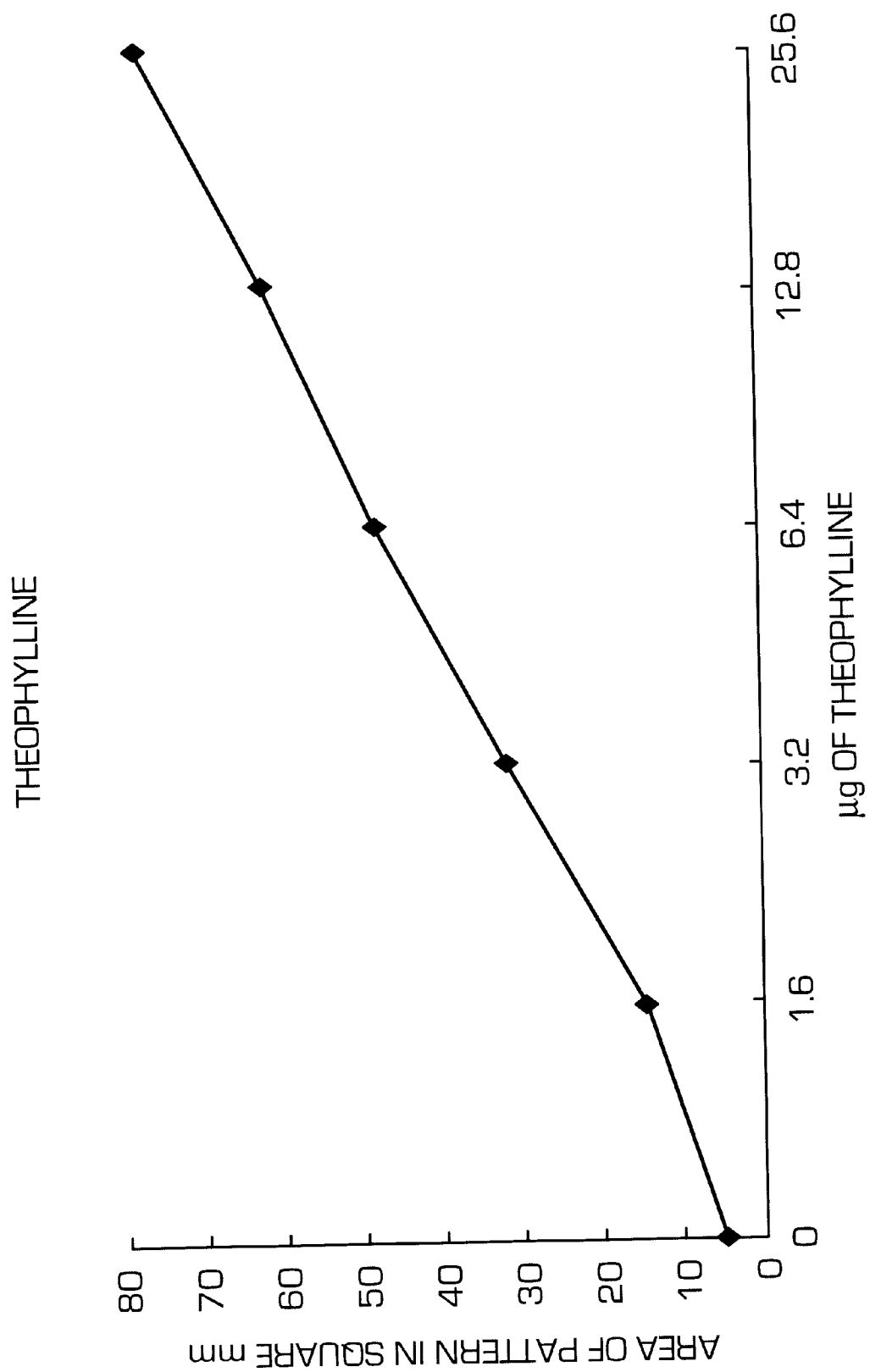
FIG. 5. is a standard curve measuring Theophylline by the solid phase diffusion assay of the present invention.

FIG. 5 shows the relationship between the area of the diffusion pattern and the concentration of unlabeled Theophylline in the test samples.

EXAMPLE IV

The following example demonstrates the solid phase diffusion assay of the present invention as used to detect low concentrations of human immunoglobulins reacting with Staphylococcal Protein A. This is an example of a "sandwich assay" based on a ligand (immunoglobulin) and receptor Protein A) interaction. Peroxidase labeled rabbit antibodies directed against the human inuntoglobulins are used as free antibodies.

The nitrocellulose paper (Bio-Rad, Rockville Centre, N.Y., No. 162-0115, 0.45 microns) is cut into pieces with a dimension of approximately 1 square inch. These pieces are than washed for 10 minutes in phosphate buffered saline (pH 7.2). The washed papers are then incubated at 4° C. for 12 hours in a phosphate buffered saline solution containing 0.01 mg/ml Staphylococcal Protein A (Pharmacia Fine Chemicals, Upsula, Sweden) and 1 mg/ml bovine serum albumin (Sigma Chemical Company, St. Louis, Mo.). After the 12 hour incubation, the papers are again washed for 10 minutes in phosphate buffered saline. The papers are then incubated for 2 hours in a 5% solution of bovine serum albumin. This incubation is performed to saturate non-specific binding sites. The glycine incubation is performed to saturate all non-specific binding sites. The papers are again washed in phosphate buffered saline. After a short wash in distilled water, the membrane pieces are air dried.

A standard curve is prepared in phosphate buffered saline containing 5% bovine serum albumin using 6 different human immunoglobulin G dilutions. The concentrations of immunoglobulin G (Boehringer, Mannheim, Germany) in the standard curve range between 32 μg/ml to 1 mg/ml. A solution containing 10 μl of each dilution was applied with a capillary tube onto the nitrocellulose paper. After the test fluid diffuses into the nitrocellulose paper, the papers are then washed for 3 minutes in a phosphate buffered saline solution containing 0.5% polyoxy-ethylenesorbitan monolaurate, sold under the trademark "TWEEN 20". Sigma Chemical Company, St. Louis, Mo.). Thereafter, peroxidase labeled antibodies specific for human IgG heavy and light chains (Dako Accurate Chemicals) are applied as a second layer of the sandwich. These labeled antibodies are diluted 1:1000 in phosphate buffered saline with 1% bovine serum albumin.

After a second washing step using phosphate buffered saline and 0.5% TWEEN 20, the papers are then submerged in a substrate solution. The substrate solution is made up as follows: 15 μg of 4-chloro-1-naphthol (Bio-Rad, Rockville Centre, N.Y., No. 170-6534) was dissolved in 5 ml of methanol. To this solution is added 25 ml of distilled water and 15 μl of 30% hydrogen peroxide. A blue circular pattern develops after several minutes.

Figure 6:
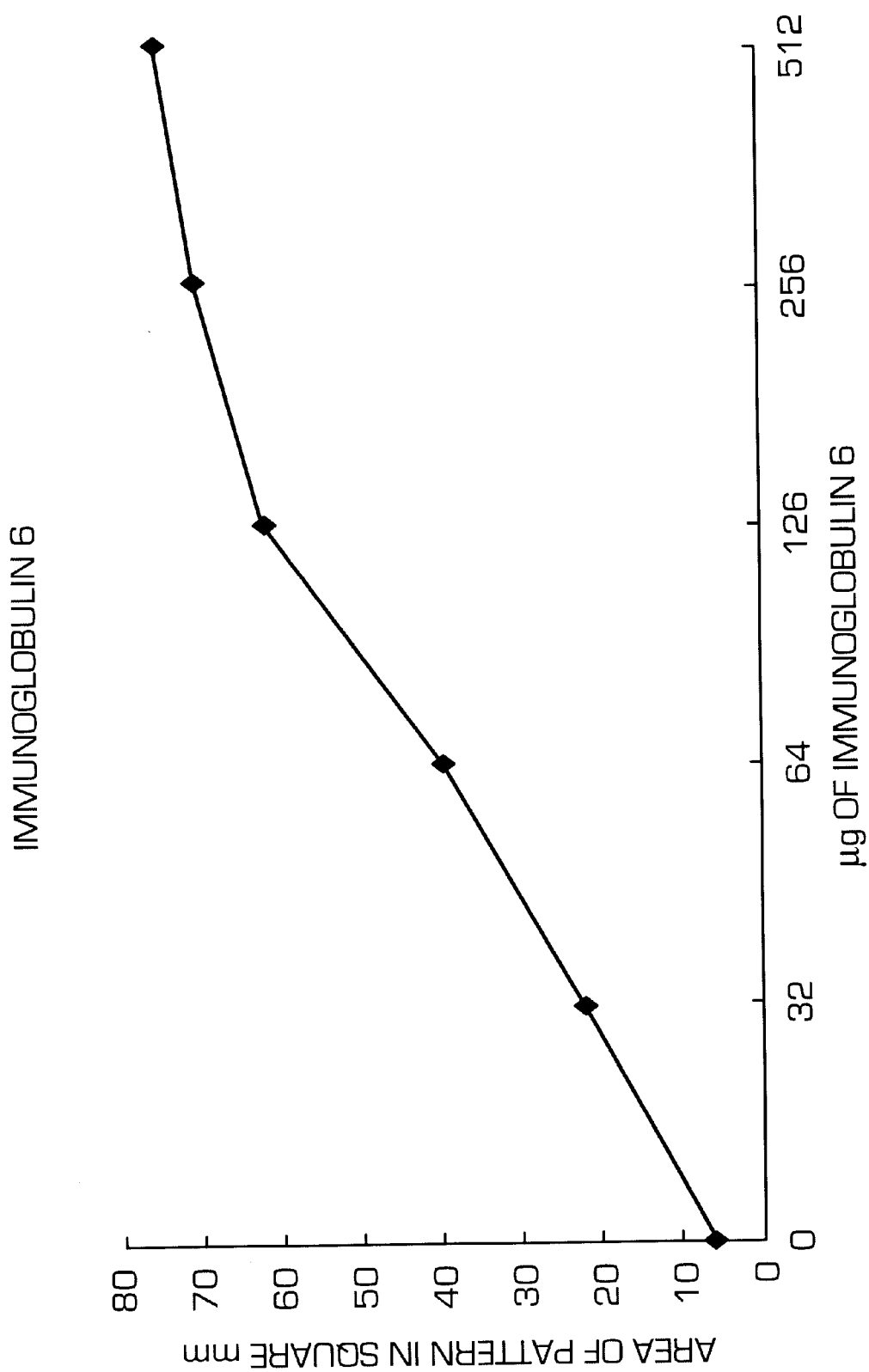
FIG. 6 is a standard curve measuring immunoglobulin g by the solid phase diffusion assay of the present invention.

As shown m FIG. 6, the area of the circular diffusion pattern is proportional to the amount of free immunoglobulins in the test solution. In accordance with the present invention, it has been found that only a single standard curve has to be run for a given batch of prepared nitrocellulose test substances and labeled antibody.

EXAMPLE V

Solid phase supports available for thin layer chromatography can be utilized in the solid phase diffusion assay of the present invention. The commercially available thin layer chromatography supports are very thin, usually about 250 microns thick and may easily be adapted to the solid phase diffusion assay of the present invention.

Anti-gentamicin antibodies are covalently bound to the solid support in the following manner. A cellulose based thin layer chromatography plate sold under the trademark "AVICEL F" (Analtech, Inc., Newark DE), is incubated overnight at 4° C. with the goat anti-gentamicin serum diluted 1:4 with phosphate buffered saline and 50 μl of glutaraldehyde per 100 ml of solution. The plate is then extensively washed with phosphate buffered saline with 1% bovine serum albumin (Sigma Chemical Company, St. Louis, Mo.) and. finally with phosphate buffered saline alone. The plate is then air dried.

The assay is performed by by adding 20 μl in four different dilutions of the gentamicin-horseradish peroxidase-orosomucoid conjugate described in Example 2 to a single point on the thin layer chromatography plate. After the solution diffuses, the enzyme substrate is added as described in the previous examples.

EXAMPLE VI

The following example shows the application of the solid-phase diffusion assay of the present invention as the final step of a multistep assay. This assay is designed to measure the concentration of human Immunoglobulin G. One μg of affinity-purified peroxidase-labeled antibody specific for human immunoglobulin G (Dako Accurate Chemicals, Westbury, N.Y.) is incubated for fifteen minutes at room temperature in 100 μl of phosphate buffered saline, 10% rabbit serum, together with 10 μl of a 1 to 1000 dilution of the test serum (diluted in phosphate buffered saline). Five μl of the test substance is then applied to the nitrocellulose coated with rabbit anti-peroxidase antibody. This nitrocellulose was prepared as described in Example I with the following difference. The rabbit immunoglobulin was diluted with normal rabbit serum so that 4 μl containing 1 μg of the above peroxidase-labeled antibody diffuses close to the edge of the diffusing solution (approximately 8 mm). Thus, in this variation of the solid phase diffusion assay of the present invention, the diffusion pattern of the reagents added with no test solution will have the largest area. If the test solution contained any human immunoglobulin G, the immunoglobulin G molecules will react with the peroxidase-labeled antibodies in the solution. Since a single immunoglobulin G specific antibody will react with more than one immunoglobulin G molecule, there is extensive crosslinking between immunoglobulin molecules as the binding reaction proceeds. Thus, large complexes of immunoglobulin G specific antibodies are formed. This crosslinking will reduce the number of free peroxidase labeled antibodies in solution and will also increase the size of diffusing complexes. Thus, the size of the diffusion pattern is markedly diminished as the concentration of human immunoglobulin G molecules in the test solution is increased. A standard curve is prepared with gradually increasing concentration of human immunoglobulin G in the test solution.

EXAMPLE VI

The following example shows the application of the solid phase diffusion assay of the present invention as used to assay as the final step of an assay to qualitatively and quantitatively analyze the end product. This approach may be chosen for a substance where no receptors of high affinity can be found, there only very special labels can be used or where a very high sensitivity may be necessary.

For example, it has proved difficult to produce an antibody with high enough affinity for this application against *Clostridium perfringens* toxin. Thus it would be difficult to perform the solid phase diffusion assay as described in Examples I–IV since the antibody to the toxin is of low affinity. This variation of the solid phase diffusion assay will allow one to perform a solid phase diffusion assay using the low affinity antibodies.

Rabbit antibodies against the toxin are labeled with peroxidase and then affinity-purified as is well known to one skilled in the art. The nitrocellulose paper is treated with antibodies specific for horseradish peroxidase. A constant amount of the peroxidase-labeled antibody is then incubated with the unknown amount of perfringens toxin. The mixture of labeled perfringens toxin antibody and unknown perfringens toxin is then applied to a single point on the insoluble support and allowed to diffuse. Thus, as in Example VI, in this variation of the solid phase diffusion assay of the present invention, the diffusion pattern of the reagents added with no test solution will have the largest area.

Since a single toxin-specific antibody will react with more than one toxin molecule, there is extensive crosslining between toxin molecules as the antibody-toxin molecules and peroxidase-labeled toxin specific antibodies. This cross-linking will therefore reduce the number of free toxin antibodies in solution and will also increase the size of diffusing complexes. Thus, when the toxin-antibody-peroxidase complexes are applied to the peroxidase-specific antibody-treated nitrocellulose paper, the size of the diffusing pattern is markedly diminished as the concentration of toxin molecules in the test solution is increased. A standard curve is prepared with gradually increasing concentration of *Clostridium perfringens* toxin in the test solution.

EXAMPLE VIII

The test sample in tie solid phase diffusion assay of the present invention can be applied to the insoluble support in several ways. The reagents and the insoluble support are prepared as in Example IV. A thin plastic sheet is prepared with a hole punched in the center of the sheet. The diameter of the hole is 2 mm. The plastic sheet is then placed on the nitrocellulose paper so that the hole is positioned approximately in the center of the nitrocellulose paper. 10 $\mu$l of test solution is placed over the hole in the plastic. The test solution diffuses through the hole in the plastic and into the nitrocellulose paper. After the diffusion is complete, the substrate is added and the diffusion pattern is measured as described in the previous Examples.

EXAMPLE IX

In this example, colloidal gold is used as a dye-type label. The use of a dye as a label in the solid phase immunoassay of the present invention has the advantage that no extra step for visualization of the label has to be performed. This example is similar to the procedure described in Example I with colloidal gold being used in place of the enzyme label.

Horseradish peroxidase is labeled with the colloidal gold according to a procedure described in J. DeMay, Colloidal Gold Probes in Immunocytochemistry, *Immunocytochemistry: Applications in Pathology and Biology*, Ed.: J. Polak, S. Van Noorden, J.Wright & Sons Ltd., London, pgs. 82–112, 1983.

Nitrocellulose paper is prepared as described in Example I. A standard curve measuring non-labeled peroxidase is then prepared as in Example I. 2 and ½ $\mu$l of non-labeled peroxidase in concentrations of 2,4,6,8 and 10 $\mu$/ml are added to the same quantity of 1 $\mu$g/ml of colloidal gold labeled peroxidase and a standard curve is established as described in Example I. The circle that indicates the diffusion of the sample is immediately visible. No subsequent incubations are required to visualize the diffusion pattern.

EXAMPLE X

A variation of the solid phase immunoassay using colloidal gold can be performed for assays where only qualitative results are required The sample containing non-labeled peroxidase is incubated with colloidal gold labeled antibody against peroxidase that is prepared as in Example IX. The sample is then applied to the nitrocellulose as in Example I and Example IX. The result is immediately visible as a spot on the nitrocellulose and the method is sensitive to within less than 1ng/mL of peroxidase.

A practical example of such a qualitative test is the following pregnancy test. A mixture of three monoclonal antibodies against the alpha subunit of human chorionic gonadotropin (HCG) is labeled with colloidal gold using the method referenced in Example IX. The nitrocellulose membrane is saturated with polyclonal antibodies against HCG which have been produced in a rabbit and which have been affinity purified in a Staphylococcal protein A column as known to one skilled in the art. The membrane is then covered with a cover having an approximately 2 mm aperture therein. A swab containing lyophilized goldlabeled anti-HCG antibodies is wetted with the sample urine which may contain HCG. The swab is then immediately brought into contact with the membrane cover. The urine diffuses from the swab through the opening in the membrane cover and into the nitrocellulose membrane. The swab is held in place for about 30 seconds and then removed. Concentrations of HCG greater 50 mIU/mL, which generally indicate a pregnancy, can be diagnosed by the presence of a red spot. Concentrations of HCG below 50 mIU/mL will not produce a visible spot.

EXAMPLE XI

The procedure of Example X was repeated, using a negative pressure (e.g. vacuum) applied to the underside of the nitrocellulose paper. The negative pressure was applied to enhance diffusion of the test solution (e.g. urine) through the nitrocellulose paper. The nitrocellulose paper was covered on both sides with adhesive tape, i.e., it was provided with a cover which limited the area of contact between the sample and the membrane. The tape had a 2 mm aperture on corresponding locations on both sides of the membrane which allowed for the concentration of the analyte-labeled antibody complex on a very small surface. The presence of the analyte could be seen as a red spot at the place of application.

EXAMPLE XII

The procedure of Example XI was repeated, using a positive pressure to enhance diffusion instead of a negative pressure. The positive pressure was produced using a 1 mL syringe containing 0.5 mL of the analyte/gold-labeled antibody mixture. The covered membrane contained corresponding 2 mm² openings in the covering on each side of the membrane. The membrane and its covering on both sides were housed in a standard sterile filter housing whose nembrane had been replaced by the above-described membrane and covering. The syringe was connected to the filter housing and the analyte/gold-labeled antibody mixture was forced through area of the membrane exposed by the corresponding openings. The presence of the analyte could be seen as a red spot at the place of application.

EXAMPLE XIII

The procedure in Example XI was repeated using a hydrophilic material to enhance diffusion instead of a negative pressure. The hydrophilic material was located adjacent to one side of the membrane covering. The analyte/gold-labeled antibody mixture was pipetted onto the area of the opening on the side opposite the hydrophilic membrane and allowed to diffuse successively through the opening, the paper, and into the hydrophilic membrane. The presence of the analyte was visualized by a red spot.

It should be understood that preceding Examples XI, XII, and XIII can be carried out using a membrane which is covered only on the side where the sample is applied. However, if only one side is covered, there will likely be greater diffusion of the. analytelgold-labeled antibody mixture.

It should also be understood that the effect of covering can be accomplished by alternate means. For example, one could use a funnel which is in direct contact with the surface of the nitrocellulose paper, which funnel has a small hole allowing for the application of the test solution onto the paper.

EXAMPLE XIV

Example XIV illustrates the use of the Solid Phase Diffusion assay for qualitative and quantitative detection of Deoxyribonucleic acid (DNA) or Ribonucleic acid (RNA). This example allows for rapid quantitation of Chlamydia trachomatis DNA in a sample.
A. Preparation of the nitrocellulose filter:

A 10 microgram/mL solution of a 0.1 kilobase DNA probe for Chlamydia trachocatis in 0.1M NaOH, 1M NaCl, 150 mM Na Citrate is heat denatured by boiling for 3 minutes and applied to 2 cm² of nitrocellulose paper (Bio-Rad as described). The paper is then floated for 10 seconds in a solution of 1M Phosphate Buffer pH 7 to neutralize the NaOH. The filter is then baked in a vacuum oven for 10 minutes at 80° C. Unreacted sites are blocked by incubation overnight in a DNA blocking buffer as described in "Molecular Cloning, a laboratory, Manual, eds. T. Maniatis, E. F. Fritsch and J. Sambroock, Cold Spring Harbor Laboratory, 1982, page 326.
B. Detection of sample nucleic acid:

Ten microliters of the sample nucleic acid is mixed with 10 microliters of 0.2 microgram/mL solution of a second Chlamydia trachomatis DNA probe in DNA blocking buffer. This second DNA probe is labeled with biotin as known to one skilled in the art. The biotin-labeled DNA probe sequences are not complementary to those of the solid phase probe. The mixture of sample nucleic acid and labeled probe is then heat denatured by boiling for 3 minutes. Five microliters of the mixture are applied with a capillary micropipette to the nitrocellulose and allowed to diffuse out radially. The biotin-labeled DNA probe is then visualized by the application on exactly the same spot with a capillary micropipette of five nacroliters of a 0.001 mg/mL solution of colloidal avid:i-gold 15 nm particles (EY laboratories, San Mateo Calif., catalogue number GA-01) in phosphate buffered saline pH 7.4. The formation of a red spot indicates the presence of Chlamydia trachomatis DNA in the sample.

While this invention has been described in detail with particular reference to preferred embodiments thereof, it will be understood that variations and modifications can be effected within the spirit and scope of the invention as described herein before and as defined in the appended claims.

EXAMPLE XV

The following example illustrates an additional effect which may occur by using the Solid Phase Diffusion Assay of the present invention: the test substance may form a precipitate (immune complex) upon conjugation with the label which does not allow for diffusion into the solid phase because of the particle size of the precipitate. The solid phase functions in this case as a filter retaining the precipitate. The phenomena of precipitation of the test substance after labeling and normal binding of the labeled test substance can occur at the same time: using colloidal gold the precipitate shows a dark brown to black color and can be washed off the membrane by careful rinsing with Phosphate Buffered Saline (PBS). The labeled test substance which was able to enter the solid phase shows a reddish color and cannot be washed off by rinsing with PBS.

Nitrocellulose membrane (Bio-Rad, No. 162-0115, 0.45 microns) is cut into 1 square inch squares and washed for 10 minutes in PBS, pH 7.2. The membrane is then incubated overnight in a mixture of two monoclonal antibodies against the Hepatitis B Surface Antigen (HBSA) (Clones HSORG 1,2, 1mg/ml each, pH 7.6). The membrane is blocked thereafter with 5% Bovine Serum Albumin in PBS pH 7.6, washed 3 times in PBS and vacuum dried.

Three complementary monoclonal antibodies (HSORG 11,12,13) are then labeled individually with 17 nm colloidal gold particles, each antibody at the pH of its Isoelectric Point using the procedure described in Example IX and the labeled antibody fractions are pooled. Ten patient sera with Elisa titers for HBSA>1:100 and ten negative sera are then tested using the following procedure: the individual squares of the membrane are prepared by putting an adhesive tape with a 3 mm hole in its middle on the top side of the solid phase and by lying the membrane on blotting paper. Thirty microliters of the 1:10 diluted serum (PBS pH 7.6) are then mixed with thirty microliters of the colloidal gold labeled antibody pool and the mixture is then immediately applied to the solid phase with the help of a Dacron swab. The positive samples produce a black precipitate on the-surface of the membrane which can be washed off with PBS. All ten positive sera produce a black dot, the ten negative sera do not produce a signal. The testing is repeated using the same series of sera but this time the sera are mixed with 30 microliters of each antibody individually. A red dot on the membrane can be seen in the case of the positive area. The dot cannot be washed off the membrane with PBS which indicates binding of the gold labeled antigen to the antibody on the solid phase. The procedure is repeated using a pool of only two colloidal gold labeled antibodies. All variations can be observed: some of the positive sera show a red dot on the membrane, some sera a black precipitate and some sera both. None of the negative sera shows a signal.

Membranes without antibodies but blocked with Bovine Serum Albumin using the same procedure as described are prepared and the above testing is repeated. The black precipitates are again obtained with these membranes, clearly indicating that the membrane is working as a filter and that no antibody has to be coated onto the membrane in order to observe this phenomenon. The red spots as produced with the individual gold labeled antibodies or mixtures of two antibodies cannot be visualized on these membranes, clearly indicating that this phenomenon needs the presence of an antibody coated to the membrane.

The above series of experiments is repeated using 0.1 micron color plastic beads instead of the colloidal gold. The beads are attached to the antibodies by a covalent linking procedure as well known to those skilled in the art. This label produces for practical purposes the same results as the colloidal gold label.

EXAMPLE XVI

This example shows the Solid Phase Diffusion Assay of the present invention in a competitive format. Thirty microliters of a crude extract of cell culture supernatant containing about 50 nanograms of HTLV III glycoprotein 24 KD (gp 24) are mixed with 15 microliters of patient serum (undiluted) and then 15 microliters of gold labeled monoclonal antibodies (clone Well 1,50 micrograms/ml, 17 nm colloidal gold particles, same labeling procedure as above) against gp 24 are added. This monoclonal antibody has been shown previously to recognize an epitope on gp 24, which is also relevant for the human immune response against HTLV III (classical competitive ELISA against positive human sera). The whole mixture is then applied with a swab on a Biorad-nitrocellulose membrane coated with an IgG cut of a high titer human reconvalescent serum (pooled sera, high anti-HTLV III titer as measured in Wellcome ELISA assay, same coating procedure as above, membrane covered with adhesive tape having a 3 mm hole as above, membrane on blotting paper). The HTLV-III antigen is trapped on the membrane during application of the mixture. Positive human sera are not producing a red spot on the membrane because they occupy the binding sites on the antigen. Negative sera can be visualized as a red spot on the place of application because the gold labeled monoclonal antibody binds to the gp 24 which is trapped on the membrane. The sensitivity of the assay can considerably be augmented by prolonging the incubation of the human serum with the crude antigen to 1 hour at 37° C.

I claim:

1. A method for qualitative or semi-quantitative determination of an analyte in a test sample, comprising:
    (a) providing a three layer device, said three layers being adapted to produce a color signal due to presence of said analyte and consisting essentially of an uppermost cover layer of a water-impermeable material having a hole therein with a diameter of approximately 1–5 mm, an intermediate insoluble porous support layer having a first substance bound thereon in a reaction zone, the hole exposing at least a part of the reaction zone, the first substance being selected from the group consisting of ligands and receptors which specifically bind to the analyte, and a layer of a hydrophilic material in contact with and positioned on the side of the insoluble porous support layer opposite the side with the cover layer, said device permitting transverse, but not substantial radial, diffusion of liquid through the reaction zone;
    (b) applying a measured amount in a range of approximately 1–50 μl of the test sample to the reaction zone through the hole, thus permitting the test sample to diffuse transversely, from one side to the other, through the reaction zone;
    (c) applying approximately 1–50 μl of a second substance to the reaction zone through the hole together with or after application of the test sample, thus permitting the second substance to diffuse transversely, from one side to the other, through the reaction zone, the second substance being selected from the group consisting of ligands and receptors which specifically bind to the first substance in competition with the analyte or which specifically bind to the analyte before or after binding to the first substance;
    in each of the applying steps, the hole in the uppermost cover layer together with the intermediate porous support layer and the layer of hydrophilic material facilitating a concentration effect by drawing the entirety of the applied test sample and the applied second substance into the part of the reaction zone exposed by the hole, whereby analyte present in the test sample and said second substance are immobilized upon contact with the reaction zone, a colloidal gold label being attached to the second substance before or after immobilization of the second substance, and the insoluble porous support layer having a porosity which permits diffusion of any unreacted colloidal gold-labelled second substance transversely therethrough; and
    (d) assessing the presence or approximate quantity of the immobilized second substance by assessment of the presence, for said qualitative determination, or intensity for said semi-quantitative determination, of a color signal generated by the immobilized colloidal gold label in the part of the reaction zone exposed by the hole.

2. The method of claim 1, wherein the test sample contains an unknown concentration of the analyte and a known concentration of the second substance, the second substance specifically binding to the immobilized first substance in competition with the analyte in the test sample.

3. The method of claim 2, wherein the second substance is a sample of the analyte conjugated to a colloidal gold label.

4. The method of claim 1, wherein the second substance specifically binds to the analyte and is applied to the reaction zone after the test sample.

5. The method of claim 1, wherein labelling of the second substance is achieved by binding the second substance to a third substance conjugated to a colloidal gold label, the third substance being selected from the group consisting of ligands and receptors which specifically bind to the second substance.

6. The method of claim 1, wherein the analyte and the ligands or receptors which bind to the analyte are selected from the group consisting of specifically interacting pairs of (a) antigens and antibodies, (b) sugars and lectins, (c) complementary nucleic acids, (d) enzymes and substrates, (e) biotin and avidin, or (f) immunoglobulin and Staphylococcal Protein A.

7. The method of claim 1, wherein the analyte is selected from the group consisting of albumin, angiotensin, bradykinin, calcitonin, carcinoembryonic antigen, chloriomamotropin, chorogonadotropin, corticotropin, erythropoietin, Factor VIII, fibrinogen, alpha-2-H globulin, follitropin, gastrin, gastrin sulfate, glucagon, gonadotropin, haptoglobin, hepatitis B surface antigen, immunoglobulins (A,D,E,G,M,), insulin, lipotropin, kallidin, melanotropin, oxytocin, pancreozymin, placental lactogen, prathryin, proangiotensin, prolactin, somatotropin, relaxin, secretin, somatomadin, somatostatin, thryrotropin, vasotocin, thymopoietin, vasopressin and alpha-1-fetoprotein.

8. The method of claim 1, wherein the intermediate insoluble porous support layer comprises nitrocellulose.

9. A kit for qualitative or semi-quantitative determination of an analyte in a measured amount of test sample of approximately 1–50 µl, comprising:
  (a) a three layer device, said three layers being adapted to produce a color signal due to presence of said analyte and consisting essentially of an uppermost cover layer of a water-impermeable material having a hole therein with a diameter of approximately 1–5 mm, an intermediate insoluble porous support layer having a first substance bound thereon in a reaction zone, the hole exposing at least a part of the reaction zone, the first substance being selected from the group consisting of ligands and receptors which specifically bind to the analyte, and a layer of a hydrophilic material in contact with and positioned on the side of the insoluble porous support layer opposite the side with the cover layer, said device permitting transverse, but not substantial radial, diffusion of liquid through the reaction zone;
  (b) a second substance attached to a colloidal gold label, the second substance being applied to the reaction zone through the hole together with or after application of the test sample, the second substance being selected from the group consisting of ligands and receptors which specifically bind to the first substance in competition with the analyte or which specifically bind to the analyte before or after binding to the first substance, and the insoluble porous support layer having a porosity which permits diffusion of any unreacted colloidal gold-labelled second substance transversely therethrough;
    in each application, the hole in the uppermost cover layer together with the intermediate porous support layer and the layer of hydrophilic material facilitating a concentration effect by drawing the applied test sample and the applied second substance into the part of the reaction zone exposed by the hole, whereby analyte present in the test sample and said second substance are immobilized upon contact with the reaction zone;
    and the colloidal gold label providing a color signal in the part of the reaction zone exposed by hole which can be assessed to determine the presence, for said qualitative determination, or by its intensity to determine an approximate quantity, for said semi-quantitative determination, of the immobilized second substance.

10. The kit of claim 9, wherein the analyte and the ligands or receptors which bind to the analyte are selected from the group consisting of specifically interacting pairs of (a) antigens and antibodies, (b) sugars and lectins, (c) complementary nucleic acids, (d) enzymes and substrates, (e) biotin and avidin, or (f) immunoglobulin and Staphylococcal Protein A.

11. The kit of claim 9, wherein the analyte is selected from the group consisting of albumin, angiotensin, bradykinin, calcitonin, carcinoembryonic antigen, chloriomamotropin, chorogonadotropin, corticotropin, erythropoietin, Factor VIII, fibrinogen, alpha-2-H globulin, follitropin, gastrin, gastrin sulfate, glucagon, gonadotropin, haptoglobin, hepatitis B surface antigen, immunoglobulins (A,D,E,G,M,), insulin, lipotropin, kallidin, melanotropin, oxytocin, pancreozymin, placental lactogen, prathryin, proangiotensin, prolactin, somatotropin, relaxin, secretin, somatomadin, somatostatin, thryrotropin, vasotocin, thymopoietin, vasopressin and alpha-1-fetoprotein.

12. The kit of claim 9, wherein the intermediate insoluble porous support layer comprises nitrocellulose.

13. A method for qualitative or semi-quantitative determination of an analyte in a test sample, comprising:
  (a) providing a three functional layer device consisting essentially of an uppermost cover layer of a water-impermeable material having a hole therein with a diameter of approximately 1–5 mm, an intermediate insoluble porous support layer having a first substance bound thereon in a reaction zone, the hole exposing at least a part of the reaction zone, the first substance being selected from the group consisting of ligands and receptors which specifically bind to the analyte, and a layer of a hydrophilic material in contact with and positioned on the side of the insoluble porous support layer opposite the side with the cover layer, said device permitting transverse, but not substantial radial, diffusion of liquid through the reaction zone;
  (b) applying a measured amount in a range of approximately 1–50 µl of the test sample to the reaction zone through the hole, thus permitting the test sample to diffuse transversely, from one side to the other, through the reaction zone;
  (c) applying approximately 1–50 µl of a second substance to the reaction zone through the hole together with or after application of the test sample, thus permitting the second substance to diffuse transversely, from one side to the other, through the reaction zone, the second substance being selected from the group consisting of ligands and receptors which specifically bind to the first substance in competition with the analyte or which specifically bind to the analyte before or after binding to the first substance;
    in each of the applying steps, the hole in the uppermost cover layer together with the intermediate porous support layer and the layer of hydrophilic material facilitating a concentration effect by drawing the entirety of the applied test sample and the applied second substance into the part of the reaction zone exposed by the hole, whereby analyte present in the test sample and said second substance are immobilized upon contact with the reaction zone, a colloidal gold label being attached to the second substance before or after immobilization of the second substance, and the insoluble porous support layer having a porosity which permits diffusion of any unreacted colloidal gold-labelled second substance transversely therethrough; and
  (d) assessing the presence or approximate quantity of the immobilized second substance by assessment of the presence, for said qualitative determination, or intensity for said semi-quantitative determination, of a color signal generated by the immobilized colloidal gold label in the part of the reaction zone exposed by the hole.

14. A kit for qualitative or semi-quantitative determination of an analyte in a measured amount of test sample of approximately 1"50 µl, comprising:
  (a) a three functional layer device consisting essentially of an uppermost cover layer of a water-impermeable material having a hole therein with a diameter of approximately 1–5 mm, an intermediate insoluble porous support layer having a first substance bound thereon in a reaction zone, the hole exposing at least a part of the reaction zone, the first substance being selected from the group consisting of ligands and receptors which specifically bind to the analyte, and a layer of a hydrophilic material in contact with and positioned on the side of the insoluble porous support layer opposite the side with the cover layer, said device permitting transverse, but not substantial radial, diffusion of liquid through the reaction zone;

(b) a second substance attached to a colloidal gold label, the second substance being applied to the reaction zone through the hole together with or after application of the test sample, the second substance being selected from the group consisting of ligands and receptors which specifically bind to the first substance in competition with the analyte or which specifically bind to the analyte before or after binding to the first substance, and the insoluble porous support layer having a porosity which permits diffusion of any unreacted colloidal gold-labelled second substance transversely therethrough;

in each application, the hole in the uppermost cover layer together with the intermediate porous support layer and the layer of hydrophilic material facilitating a concentration effect by drawing the applied test sample and the applied second substance into the part of the reaction zone exposed by the hole, whereby analyte present in the test sample and said second substance are immobilized upon contact with the reaction zone;

and the colloidal gold label providing a color signal in the part of the reaction zone exposed by hole which can be assessed to determine the presence, for said qualitative determination, or by its intensity to determine an approximate quantity, for said semi-quantitative determination, of the immobilized second substance.

* * * * *